(12) United States Patent
O'Hara (10) Patent No.: US 10,463,704 B2
(45) Date of Patent: *Nov. 5, 2019

(54) COMPOSITION COMPRISING LACTOBACILLUS PLANTARUM

(71) Applicant: OPTIBIOTIX LIMITED, Heslington, York (GB)

(72) Inventor: Stephen Patrick O'Hara, York (GB)

(73) Assignee: OPTIBIOTIX LIMITED, Heslington, York (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/034,492

(22) PCT Filed: Nov. 5, 2014

(86) PCT No.: PCT/GB2014/053301
§ 371 (c)(1),
(2) Date: May 4, 2016

(87) PCT Pub. No.: WO2015/067947
PCT Pub. Date: May 14, 2015

(65) Prior Publication Data
US 2016/0287645 A1    Oct. 6, 2016

(30) Foreign Application Priority Data

Nov. 5, 2013 (GB) .................................. 1319540.9

(51) Int. Cl.
A61K 35/747 (2015.01)
C12N 1/20 (2006.01)
A23L 33/135 (2016.01)

(52) U.S. Cl.
CPC .......... *A61K 35/747* (2013.01); *A23L 33/135* (2016.08); *C12N 1/20* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,214,336 B1 * | 4/2001 | Bukowska ............ | A61K 35/747 424/93.45 |
| 2004/0126356 A1 * | 7/2004 | Pang .................... | A61K 35/741 424/85.1 |
| 2008/0254011 A1 | 10/2008 | Rothschild et al. | |
| 2009/0214594 A1 | 8/2009 | Fichot et al. | |
| 2011/0117629 A1 * | 5/2011 | Lin ........................ | C12N 1/20 435/252.9 |
| 2011/0177044 A1 | 7/2011 | Thomas et al. | |
| 2011/0206649 A1 | 8/2011 | Bergonzelli Degonda et al. | |
| 2012/0213753 A1 * | 8/2012 | Cune Castellana .... | A61K 35/74 424/93.45 |
| 2012/0263696 A1 | 10/2012 | Roos | |
| 2016/0271191 A1 * | 9/2016 | O'Hara .................. | A23L 33/10 |
| 2018/0289749 A1 * | 10/2018 | O'Hara .................. | A61P 9/12 |
| 2018/0303857 A1 * | 10/2018 | O'Hara .................. | A23L 33/30 |
| 2018/0318364 A1 * | 11/2018 | O'Hara .................. | A61K 35/74 |

FOREIGN PATENT DOCUMENTS

| | | |
|---|---|---|
| EP | 0 856 259 A1 | 8/1998 |
| EP | 2 216 036 A1 | 8/2010 |
| WO | 2004/074496 A1 | 9/2004 |
| WO | 2010/124387 A1 | 11/2010 |

OTHER PUBLICATIONS

Nguyen et al. 2007 (Characterization of Lactobacillus plantarum PH04, a potential probiotic bacterium with cholesterol lowering effects; International Journal of Food Microbiology 113:358-361).*
Eyre-Walker et al. 2007 (The distribution of fitness effects of new mutations; Nature Reviews, vol. 8: 610-618).*
Bukowska et al. 1998 (Decrease in fibrinogen and LDL-cholesterol levels upon supplementation of diet with Lactobacillus plantarum in subject with moderately elevated cholesterol; Atherosclerosis 137: 437-438).*
Jones et al. 2004 (Microencapsulated Genetically Engineered Lactobacillus plantarum 80 (pCBH1) for Bile Acid Deconjugation and Its implication in Lowering Cholesterol; Journal of Biomedicine and Biotechnology 2004:1:61-69) (Year: 2004).*
Nguyen et al. 2007 (Characterization of Lactobcillus plantarum PH04, a potential probiotic bacterium with cholestrol-lowering effects ; International Journal of Food Microbiology 113: 358-361). (Year: 2007).*
Guo et al. 2011 (Cholesterol Removal by Lactobacillus plantarum isolated from homemade fermented cream in inner Mongolia of China; Czech Journal of Food Science 29(3): 219-225) (Year: 2011).*
De Vries et al. 2006 (Lactobacillus plantarum—survival, functional and potential probiotic properties in the human intestinal tract; International Dairy Journal 16: 1018-1028) (Year: 2006).*
Crookes et al. 1997 (Practice nurses and the prevention of cardiovascular disease and stroke: a literature review to promote evidence-based practice. Part II: hypertension, raised blood cholesterol lack of exercise and obesity; Clinical Effectiveness in Nursing: 1: 198-205). (Year: 1997).*
International Search Report and Written Opinion issued in corresponding International Application No. PCT/GB2014/053303 dated Feb. 4, 2015.
International Search Report and Written Opinion issued in corresponding International Application No. PCT/GB2014/053290 dated Feb. 4, 2015.
International Search Report and Written Opinion issued in corresponding International Application No. PCT/GB2014/053301 dated Feb. 4, 2015.
International Search Report and Written Opinion issued in corresponding International Application No. PCT/GB2014/053302 dated Feb. 4, 2015.

(Continued)

*Primary Examiner* — Mary Maille Lyons
(74) *Attorney, Agent, or Firm* — Christopher S. Dodson; Nexsen Pruet, PLLC (57) ABSTRACT

The present invention relates to strain of *Lactobacilli* and compositions containing the strain for use in modifying the absorption of cholesterol in an individual or the treatment of heart disease, diabetes or obesity.

16 Claims, 9 Drawing Sheets

(56) References Cited

OTHER PUBLICATIONS

Al-Fataftah, A. et al., "Enrichment of vitamin B12 and B6 and lowering cholesterol levels of eggs by lactic acid bacteria", International Journal of Food, Agriculture & Environment, vol. 11, No. 2, Jan. 1, 2013, pp. 674-678, XP55158928, Helsinki, ISSN: 1459-0255.

Al-Fataftah, A. et al., "Administration of lactic acid bacteria to enhance synthesis of vitamin B12 and B6 and lower cholesterol levels in poultry meat", International Journal of Food, Agriculture & Environment, vol. 11, No. 2, Jan. 1, 2013, pp. 604-609, XP55158929, Helsinki, ISSN: 1459-0255.

Kumar R., et al., "Bile Salt Hydolase (Bsh) Activity Screening of Lactobacilli: In vitro Selection of Indigenous Lactobacillus Strains with Potential Bile Salt Hydrolysing and Cholesterol-Lowering Ability", Probiotics and Antimicrobial Proteins, vol. 4, No. 3, Sep. 1, 2012, pp. 162-172, XP002734609.

Liong, M.T. et al., "Bile salt deconjugation ability, bile salt hydrolase activity and cholesterol co-precipitation ability of lactobacilli strains", International Dairy Journal, Elsevier Applied Science, Barking, GB, vol. 15, No. 4, Apr. 1, 2005, pp. 391-398, XP004715114, ISSN: 0958-6946.

Pereira, D.I.A., et al., "An in Vitro Study of the Probiotic Potential of a Bile-Salt-Hydrolyzing Lactobacillus fermentum Strain, and Determination of Its Cholesterol-Lowering Properties", Applied and Environmental Microbiology, vol. 69, No. 8, Aug. 1, 2003, pp. 4743-4752, XP055163574, ISSN: 0099-2240.

Rabiu, B.A., et al., "Synthesis and fermentation properties of novel galacto-oligosaccharides by beta-galactosidases from *Bifidobacterium* species", Applied and Environmental Microbiology, American Society for Microbiology, US, vol. 67, No. 6, Jun. 1, 2001, pp. 2526-2530, XP002613005, ISSN: 0099-2240.

Splechtna, B., et al., "Production of Prebiotic Galacto-Oligosaccharides from Lactose Using [beta]-Galactosidases from Lactobacillus reuteri", Journal of Agricultural and Food Chemistry, vol. 54, No. 14, Jul. 1, 2006, pp. 4999-5006, XP0055161581, ISSN: 0021-8561.

Tzortzis, G. et al. "In vitro evaluation of the fermentation properties of galactooligosaccharides synthesized by [alpha]-galactosidase from Lactobacillus Reuteri", Applied Microbiology and Biotechnology, Springer, DE, vol. 64, No. 1, Jan. 1, 2004 (Jan. 1, 2004), pp. 106-111, XP002285616, ISSN: 0175-7598, DOI: 10.1007/S00253-003-1427-Z.

Park, Yoo Heon et al. "Effect of Dietary Inclusion of Lactobacillus acidophilus ATCC 43121 on Cholesterol Metabolism in Rats", Journal of Microbiology and Biotechnology, vol. 17, No. 4, Apr. 1, 2007 (Apr. 1, 2007), pp. 655-662, XP002734586, Seoul, Korea ISSN: 1017-7825.

Noh, D. O. et al. "Incorporation of Cholesterol into the Cellular Membrane of Lactobacillus acidophilus ATCC 43121", Journal of Dairy Science, American Dairy Science Association, US, vol. 80, No. 12, Dec. 1, 1997 (Dec. 1, 1997), pp. 3107-3113, XP027048111, ISSN: 0022-0302.

\* cited by examiner

COMPOSITION COMPRISING LACTOBACILLUS PLANTARUM

CROSS REFERENCE TO RELATED APPLICATIONS

This application is a U.S. National Phase of PCT/GB2014/053301, filed Nov. 5, 2014, which claims priority to Great Britain Application No. 1319540.9, filed Nov. 5, 2013, each of which is incorporated herein by reference in its entirety.

TECHNICAL FIELD OF THE INVENTION

The invention relates to a probiotic composition which is useful in the management of cholesterol levels.

BACKGROUND TO THE INVENTION

Probiotics are bacteria which confer health benefits to a host. Typically, cultures of probiotic bacterial strains are consumed or administered to individuals in order to supplement the naturally occurring bacteria population of the gut. A number of health benefits have been associated with probiotics, including reducing the incidence of cancer, diarrhoea and irritable bowel syndrome to name a few. Probiotics have the potential to help in the management in a number of physiological conditions and act to reduce the absorption of certain ingested substances, such as lipids. Preliminary studies also indicate that probiotics can be useful in reducing serum levels of cholesterol and blood pressure and help modulate diabetes and reduce weight.

It is an object of the present invention to provide a probiotic composition which can already reduce the absorption of cholesterol in the gut. It would also be beneficial if the probiotic composition could also be used to treat other physiological conditions, such as heart disease, diabetes or obesity.

SUMMARY OF THE INVENTION

In one aspect of the present invention, there is provided a composition comprising at least one of the strains selected from *Lactobacillus plantarum* 2828 (ECGC 13110403); *Lactobacillus plantarum* 2830 (ECGC 13110402); and *Lactobacillus plantarum* 2691 (ECGC 13110401), or mutant strains thereof for use in the modification of the absorption of cholesterol.

In a second aspect of the present invention, there is provided a composition comprising at least one of the strains selected from *Lactobacillus plantarum* 2828 (ECGC 13110403); *Lactobacillus plantarum* 2830 (ECGC 13110402); and *Lactobacillus plantarum* 2691 (ECGC 13110401), or mutant strains thereof for use in the treatment of high cholesterol, heart disease, diabetes or obesity.

In a further aspect of the present invention, there is provided the use of a composition comprising at least one of the strains selected from *Lactobacillus plantarum* 2828 (ECGC 13110403); *Lactobacillus plantarum* 2830 (ECGC 13110402); and *Lactobacillus plantarum* 2691 (ECGC 13110401), or mutant strains thereof, in the manurfacture of a medicament for the treatment of high cholesterol, heart disease, diabetes or obesity.

The term "mutant strain" in the context of this patent application is intended to mean any strains which are directly derived from those strains disclosed, but which are phenotypically different due to the introduction of one or more genetic mutations (whether by genetic engineering or selection).

The compositions of the present inventions are primarily aimed at modifying the absorption of cholesterol or the treatment of certain related diseases in human individuals. However, the compositions may equally be used to treat animals.

In common with both aspects, the composition may further comprise the strain *Lactobacillus acidophilus* ATCC 43121 or mutant strains thereof.

Furthermore, the composition may comprise two or more strains selected from *Lactobacillus plantarum* 2828 (ECGC 13110403); *Lactobacillus plantarum* 2830 (ECGC 13110402); and *Lactobacillus plantarum* 2691 (ECGC 13110401); *Lactobacillus acidophilus* ATCC 43121 or mutant strains thereof.

The strain or strains may be mixed with a prebiotic composition, such as an oligosaccharide. The precise prebiotic selected will, however be determined by the strain or strains within the composition and will preferably be specific for the growth of the strain or strains.

The probiotic composition will preferably be present in the composition in an effective amount so as to elicit a change in the absorption profile of cholesterol in the small intestine. Preferably, the cultures will be administered to an individual in an amount in the range of $10^5$ cfu/g to $10^{12}$ cfu/g. More preferably, the probiotic bacterial strain is in an amount in the range of $10^8$ cfu/g to $10^9$ cfu/g. Although it will be appreciated that different dosages may be administered depending upon the individuals' condition.

The strain may be encapsulated. Many encapsulation techniques will be apparent to the skilled addressee and the one employed will be tailored to the required stability of the probiotic culture during digestive transit. The encapsulate may comprise a prebiotic specifically tailored to the probiotic The probiotic composition may further comprise an excipient or carrier compound to enable it to be released at the most appropriate time in for reducing cholesterol absorption. Typically, the culture must survive relatively intact until it reaches the intestinal enterocytes of the small intestine.

The composition may be in a number of food stuff formats, such as a drinkable liquid, a spread and/or powder which can be mixed with a solid or liquid food stuff. It may also be provided as a dietary supplement.

The composition may be combined with one or more active ingredients, such as vitamins, minerals, phytochemicals, antioxidants, and combinations thereof.

Vitamins may include fat soluble vitamins such as vitamin A, vitamin D, vitamin E, and vitamin and combinations thereof. In some embodiments, vitamins can include water soluble vitamins such as vitamin C (ascorbic acid), the B vitamins (thiamine or B 1, riboflavoin or B25 niacin or B3, pyridoxine or B6, folic acid or B9, cyanocobalimin or B12, pantothenic acid, biotin), and combinations thereof.

Minerals may include but are not limited to sodium, magnesium, chromium, iodine, iron, manganese, calcium, copper, fluoride, potassium, phosphorous, molybdenum, selenium, zinc, and combinations thereof.

Antioxidants may include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

Phytochemicals may include but are not limited to carotenoids, chlorophyll, chlorophyllin, fiber, flavanoids, anthocyamns, cyaniding, delphinidin, malvidin, pelargonidin, peonidin, petunidin, flavanols, catechin, epicatechin, epigallocatechin, epigailocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

Alternative (or additionally) to a pharmaceutical or medicament, the composition may be used as a dietary supplement, a nutraceutical or a functional food. Furthermore, the composition could be incorporated into an existing food stuffs, such as yoghurt, food spread or as a powder which can be easily blended with foodstuffs or made into a liquid drink.

In accordance with yet a third aspect of the present invention, there is provided a method of treating an individual with elevated cholesterol serum levels by administering a composition having an effective amount of at least one of the strains selected from Lactobacillus plantarum 2828 (ECGC 13110403); Lactobacillus plantarum 2830 (ECGC 13110402); and Lactobacillus plantarum 2691 (ECGC 13110401), or mutant strains thereof.

The method may further comprise additionally administering the strain Lactobacillus acidophilus ATCC 43121 or mutant strains thereof.

The method may comprise administering two or more strains selected from Lactobacillus plantarum 2828 (ECGC 13110403); Lactobacillus plantarum 2830 (ECGC 13110402); and Lactobacillus plantarum 2691 (ECGC 13110401); Lactobacillus acidophilus ATCC 43121 or mutant strains thereof.

It will be apparent to the skilled addressee that a number of the features of the composition listed in respect to the first and second aspects of the invention will be interchangeable with the composition administered in the present method.

DETAILED DESCRIPTION OF THE INVENTION

Embodiments of the present invention will now be described, by way of example only in which.

An initial high throughput screening (HTS) trial of 718 strains of Lactobacilli was conducted to assess the resistance to different types of bile salts. Further experiments were then conducted to investigate bile precipitation in 286 resistant strains in order to establish bile salt hydrolase activity.

The strains tested were: Lactobacilli acidophilus, Lactobacilli helveticus, Lactobacilli alimentarius, Lactobacilli brevis, Lactobacilli buchneri, Lactobacilli casei (including subspecies: rhamnosus, casei, tolerans, pseudoplantarum, paracasei, alactotsus and rhamnosus), Lactobacilli crispatus, Lactobacilli curvatus (including subspecies: curvatus), Lactobacilli delbrueckii (including subspecies: bulgaricus and lactis), Lactobacilli fermentum, Lactobacilli panis, Lactobacilli paracasei (including subspecies: paracasei), Lactobacilli pentosus, Lactobacilli planatarum, Lactobacilli plantarum, Lactobacilli rhamnosus, Lactobacilli sakei, Lactobacilli salivarius (including subspecies: salivarius).

Strains were grown overnight in MRS at 37° C. Of these cultures glycerol stocks were made and stored at −80° C. A microtiterplate was inoculated and all strains were placed in quadriplicate into masterplates.

The bile salts used in these experiments were purchased from Sigma® and were as follows: Sodium glycodeoxycholate (GDCA) (Sigma product number G3258, CAS: 16409-34-0); sodium taurodeoxycholate hydrate (TDCA) (Sigma product number T0875, CAS: 207737-97-1) and Bile bovine (Oxgal) (Sigma product number B3883, CAS: 8008-63-7). The concentrations of the bile salts used in the experiments were as follows: 0.5% GDCA; 0.5% TDCA; 0.5% oxgal; and 2.0% oxgal. In vitro data using glycodeoxycholate is believed to be more likely to reflect the likelihood of product efficacy as it more closely mimics the in vivo human environment.

Overnight cultures were grown in 96 well plates in MRSA at 37° C. Then 5 µl of the cultures spotted into wells containing 150 µl MRSA agar with added bile salts in 96 well plates and incubated for 48 hours under aerobic/anaerobic conditions. pH conditions were monitored so as to ensure proper growth of the strains.

The results showed that certain strains do grow on the MRSA plates under both anaerobic and aerobic conditions. Table 1 below shows all of the positive results from the initial HTS where a particular strain is capable of growing (assessed by measurement of $OD_{600}$) on a range of bile salts under anaerobic conditions:

TABLE 1

| Lactobacilli species/strain | Average of 0.5% TDCA-24 h | Average of 0.5% TDCA-72 h | Average of 0.5% GDCA-24 h | Average of 0.5% GDCA-72 h | Average of 0.5% Oxgal-24 h | Average of 0.5% Oxgal-72 h | Average of 2.0% Oxgal-24 h | Average of 2.0% Oxgal-72 h |
|---|---|---|---|---|---|---|---|---|
| Lactobacillus brevis | Y | Y | Y | Y | Y | Y | Y | Y |
| 293 | Y | Y | Y | Y | Y | Y | Y | Y |
| 306 | Y | Y | Y | Y | Y | Y | Y | Y |
| 1692 | Y | Y | Y | Y | Y | Y | Y | Y |
| Lactobacillus casei | Y | Y | Y | Y | Y | Y | Y | Y |
| 262 | Y | Y | Y | Y | Y | Y | Y | Y |
| 1694 | Y | Y | Y | Y | Y | Y | Y | Y |
| Lactobacillus plantarum | Y | Y | Y | Y | Y | Y | Y | Y |
| 1683 | Y | Y | Y | Y | Y | Y | Y | Y |
| 2258 | Y | Y | Y | Y | Y | Y | Y | Y |
| 2471 | Y | Y | Y | Y | Y | Y | Y | Y |
| 2472 | Y | Y | Y | Y | Y | Y | Y | Y |
| 2475 | Y | Y | Y | Y | Y | Y | Y | Y |
| 2478 | Y | Y | Y | Y | Y | Y | Y | Y |
| 2480 | Y | Y | Y | Y | Y | Y | Y | Y |
| 2481 | Y | Y | Y | Y | Y | Y | Y | Y |
| 2487 | Y | Y | Y | Y | Y | Y | Y | Y |
| 2490 | Y | Y | Y | Y | Y | Y | Y | Y |
| 2491 | Y | Y | Y | Y | Y | Y | Y | Y |
| 2492 | Y | Y | Y | Y | Y | Y | Y | Y |
| 2534 | Y | Y | Y | Y | Y | Y | Y | Y |
| 2536 | Y | Y | Y | Y | Y | Y | Y | Y |
| 2819 | Y | Y | Y | Y | Y | Y | Y | Y |
| 2826 | Y | Y | Y | Y | Y | Y | Y | Y |
| 2828 | Y | Y | Y | Y | Y | Y | Y | Y |
| 2830 | Y | Y | Y | Y | Y | Y | Y | Y |
| 2831 | Y | Y | Y | Y | Y | Y | Y | Y |
| 2832 | Y | Y | Y | Y | Y | Y | Y | Y |
| 4038 | Y | Y | Y | Y | Y | Y | Y | Y |
| 299 (1837) | Y | Y | Y | Y | Y | Y | Y | Y |
| AbBio | Y | Y | Y | Y | Y | Y | Y | Y |
| WCFS1 (1836) | Y | Y | Y | Y | Y | Y | Y | Y |
| Lactobacillus salivarius ssp. Salivarius | Y | Y | Y | Y | Y | Y | Y | Y |
| NCIMB 30225 | Y | Y | Y | Y | Y | Y | Y | Y |

Figure 1:
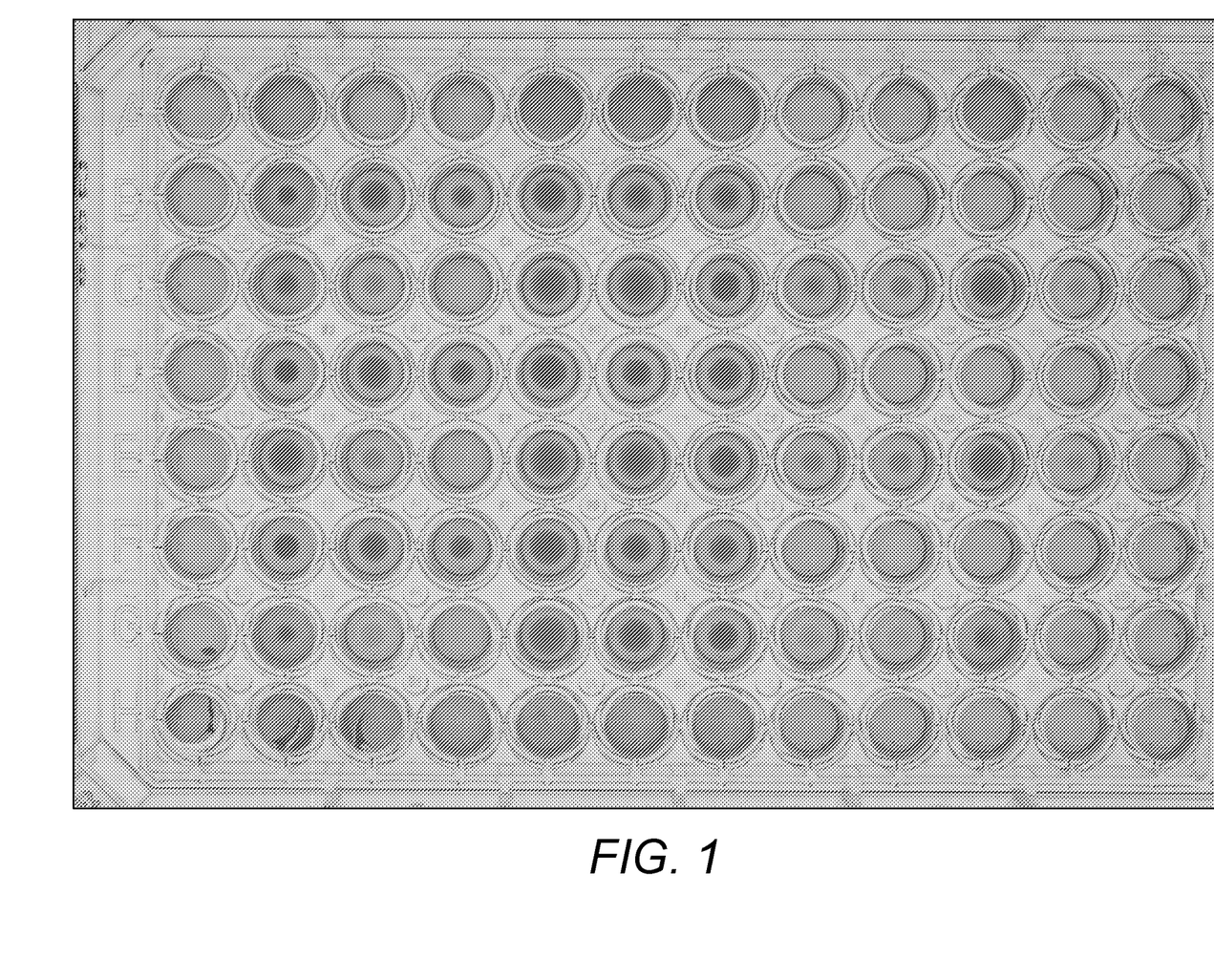
FIG. 1 is a photograph of Lactobacilli strains gown in MRSA on a 96 well plate under aerobic conditions.
Figure 2:
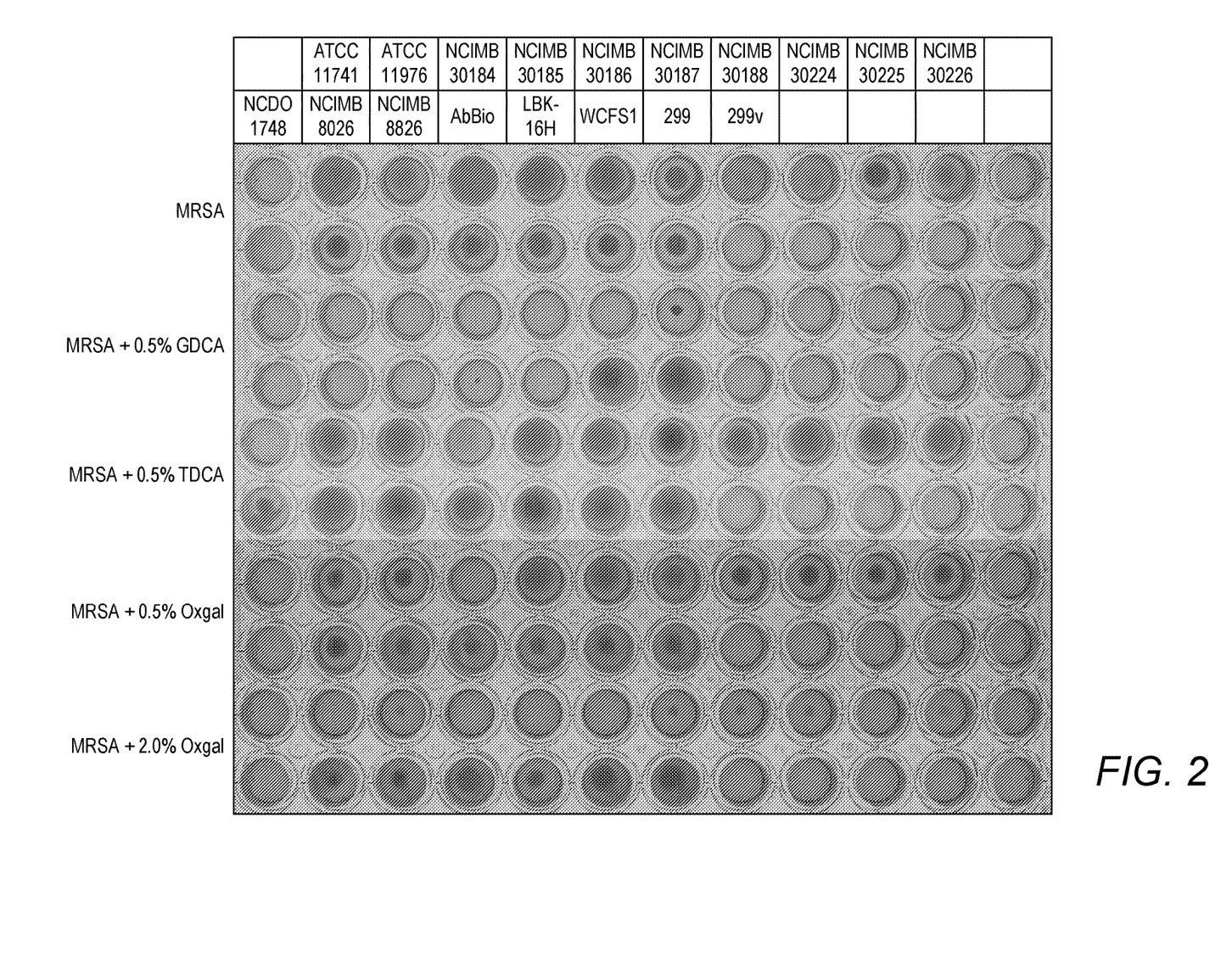
FIG. 2 is a Photograph of Lactobacilli strains grown on a 96 well plate under anaerobic conditions, the strains being grown in MRSA only (control), MRSA+0.5% GDCA, MRSA+0.5% TDCA, MRSA+0.5% Oxgal; and MRSA+2% Oxgal.
Figure 3:
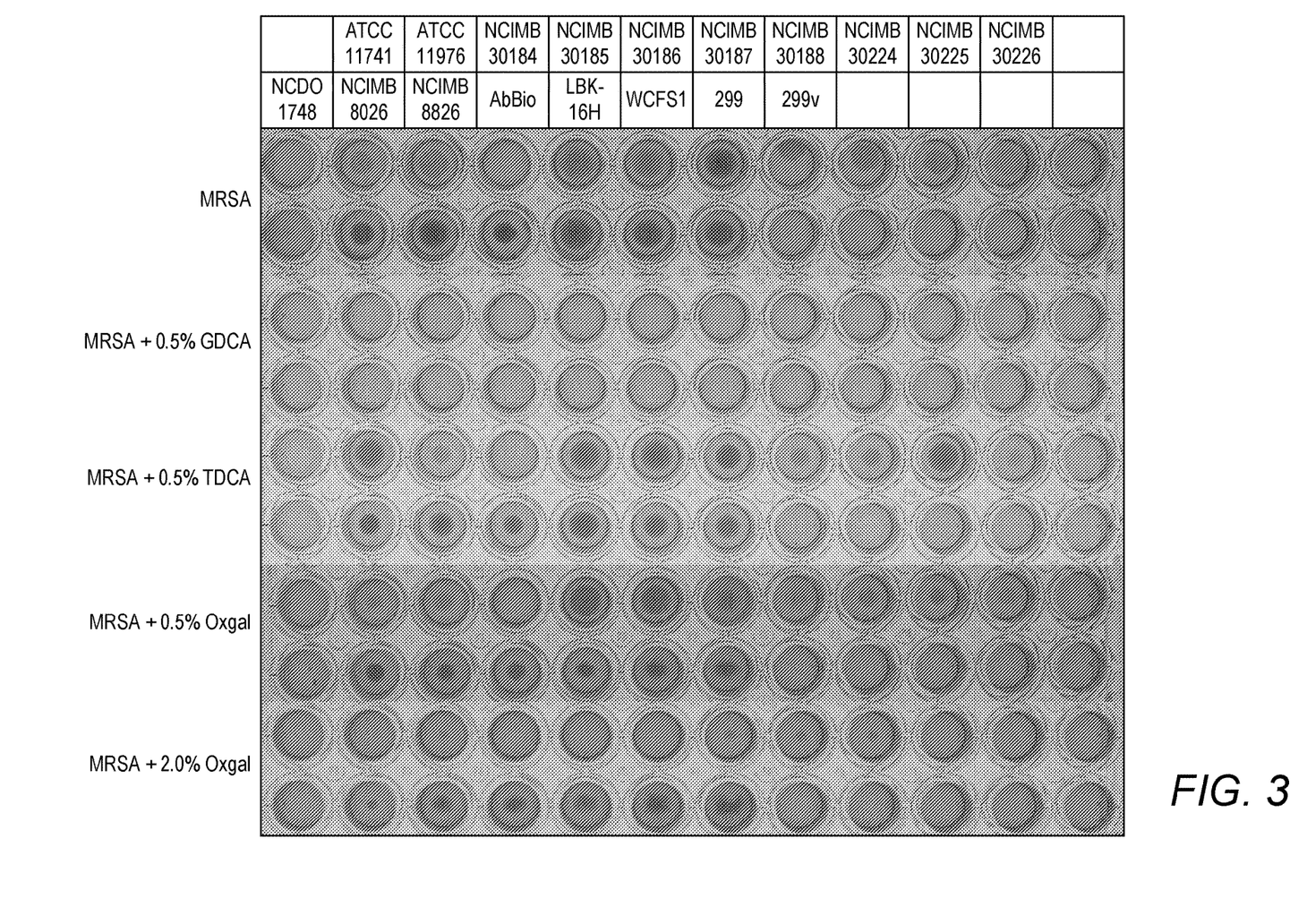
FIG. 3 is a photograph of Lactobacilli strains grown on a 96 well plate under aerobic conditions, the strains being grown in MRSA only (control), MRSA+0.5% GDCA, MRSA+0.5% TDCA, MRSA+0.5% Oxgal; and MRSA+2% Oxgal.

FIG. 1 illustrates that many strains grow well in MRSA under aerobic conditions. As shown in FIG. 3, GDCA inhibits growth of the strains in all cases under aerobic conditions but as shown in FIG. 2 under anaerobic conditions some strains do grow in GDCA. 2.0% Oxgal was found to inhibit the growth of some strains in both aerobic and anaerobic conditions.

Table 2 below shows a brief summary of the growth results:

TABLE 2

| Media | Strains grown at 20/72 hours |
|---|---|
| 0.5% TDCA | 163/208 |
| 0.5% GDCA | 38/45 |
| 0.5% Oxgal | 116/160 |
| 2.0% Oxgal | 84/103 |

A total of 41 strains were found to grow with the presence of all three bile salts present at 0.5%.

Bile salt hydrolase activity in resistant strains was then assessed by spotting 5 µl into "PCR tube plate" (150 µl of agar in a thin walled microcentrifuge tubes). These tube plates were grown under the same conditions as the 96 well plates (MRS+0.5% TDCA, MRS+0.5% GDCA, MRS+0.5% oxgal, MRS+2.0% oxgal. MRS without bile (control)).

The plates were incubated anaerobically at 37° C. and bile precipitation (related to bile salt hydrolase activity) was assessed after 24 and 48 h using the following scoring system: Record growth as + or − for BSH activity. The positives were then selected for subsequent streaking onto MRS plates containing 0.5% oxgal.

After 72 hours, a few positives had been identified. The positive cultures only showed precipitation in GDCA and TDCA.

Figure 4:
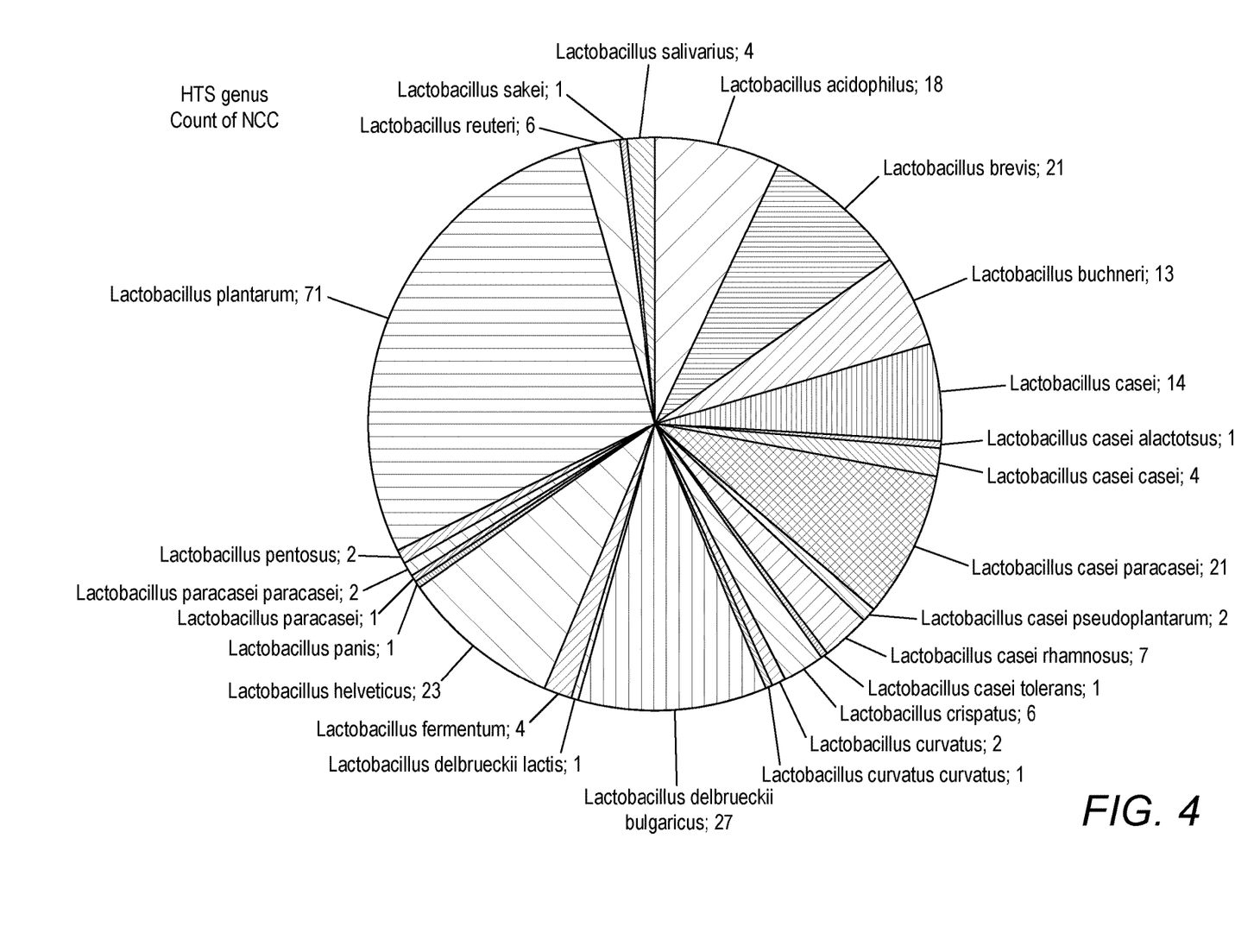
FIG. 4 is a pie chart showing the diverse range of Lactobacilli strains which underwent high throughput screening.

FIG. 4 shows the range of strains used in the initial high throughput screening assay.

After narrowing down the number of strains to 24 based on earlier BSH activity, further screening of the cholesterol assimilation in MRS medium supplemented with 0.4% was conducted.

Table 3 below shows the results of the selected strains and their average % cholesterol reduction.

TABLE 3

| Strain | Biological replicate 1 OD after 24 hours growth | Biological replicate 2 OD after 24 hours growth | Biological replicate 1 Cholesterol in mg/l | Biological replicate 2 Cholesterol in mg/l | Biological replicate 1 % cholesterol reduction | Biological replicate 2 % cholesterol reduction | Average % cholesterol reduction |
|---|---|---|---|---|---|---|---|
| 306 | 1.58 | 1.45 | 21.0 | 19.6 | 5.7 | 12.0 | 8.9 |
| 2490 | 1.31 | 1.28 | 19.1 | 21.5 | 14.4 | 3.7 | 9.1 |
| 2471 | 1.55 | 1.53 | 19.7 | 19.4 | 11.4 | 13.1 | 12.2 |
| 2475 | 0.72 | 0.75 | 19.1 | 20.0 | 14.4 | 10.4 | 12.4 |
| 2478 | 1.56 | 1.5 | 19.0 | 19.2 | 14.7 | 14.0 | 14.3 |
| 2480 | 1.2 | 1.04 | 19.3 | 18.3 | 13.4 | 18.0 | 15.7 |
| 1708 | 2.2 | 1.9 | 18.1 | 19.4 | 18.7 | 13.1 | 15.9 |
| 2472 | 1.66 | 1.95 | 19.0 | 17.6 | 14.9 | 21.0 | 17.9 |
| 2260 | 3.52 | 3.62 | 11.5 | 11.3 | 48.2 | 49.1 | 48.7 |
| ATCC 11976 | 1.37 | 1.44 | 2.63 | 6.77 | 71.5 | 26.8 | 49.2 |
| 293 | 3.54 | 3.27 | 10.8 | 11.4 | 51.7 | 48.7 | 50.2 |
| 1836 | 3.61 | 3.75 | 9.7 | 12.3 | 56.3 | 44.6 | 50.5 |
| 1837 | 3.6 | 3.72 | 10.1 | 10.0 | 54.4 | 54.9 | 54.7 |
| 2481^ | 1.45 | 1.42 | 1.0 | 18.4 | 95.4 | 17.3 | 56.3 |
| 1683 | 4.28 | 3.92 | 10.6 | 8.6 | 52.4 | 61.3 | 56.9 |
| 2535 | 2.65 | 2.62 | 9.1 | 8.1 | 59.3 | 63.5 | 61.4 |
| ATCC 11741 | 1.24 | 1.33 | 3.43 | 3.50 | 62.9 | 62.1 | 62.5 |
| 2826 | 3.28 | 4.36 | 7.3 | 6.8 | 67.0 | 69.4 | 68.2 |
| 2691 | 3.12 | 2.68 | 7.1 | 5.7 | 68.2 | 74.4 | 71.3 |
| ATCC 43121 | 3.15 | 4.52 | 6.4 | 4.4 | 71.4 | 80.1 | 75.7 |
| 2831 | 3.75 | 3.81 | 4.5 | 5.5 | 79.6 | 75.4 | 77.5 |
| 2830 | 3.22 | 2.84 | 5.3 | 4.5 | 76.1 | 79.7 | 77.9 |
| 2828 | 3.4 | 3.02 | na** | 4.0 |  | 82.2 | 82.2 |
| NCIMB30187 | 2.75 | 2.58 | 3.5 | 4.3 | 84.4 | 80.8 | 82.6 |

Figure 5:
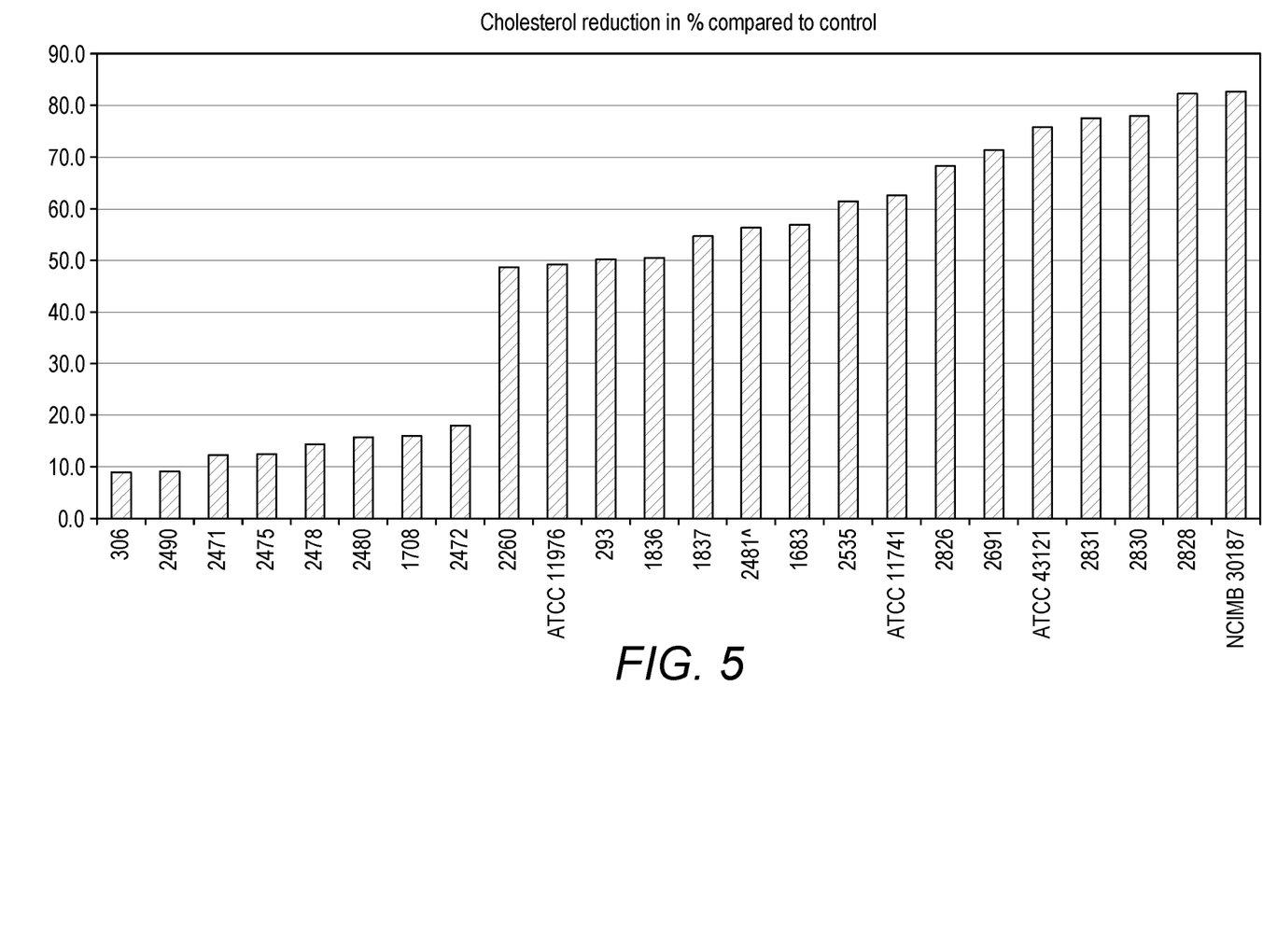
FIG. 5 is a bar chart showing the results of the 24 strains which were identified for further analysis of their cholesterol reducing ability.

FIG. 5 shows the results of the table in a bar chart and illustrates that there is a big difference between the first 8 strains compared to the rest of the strains.

Figure 6:
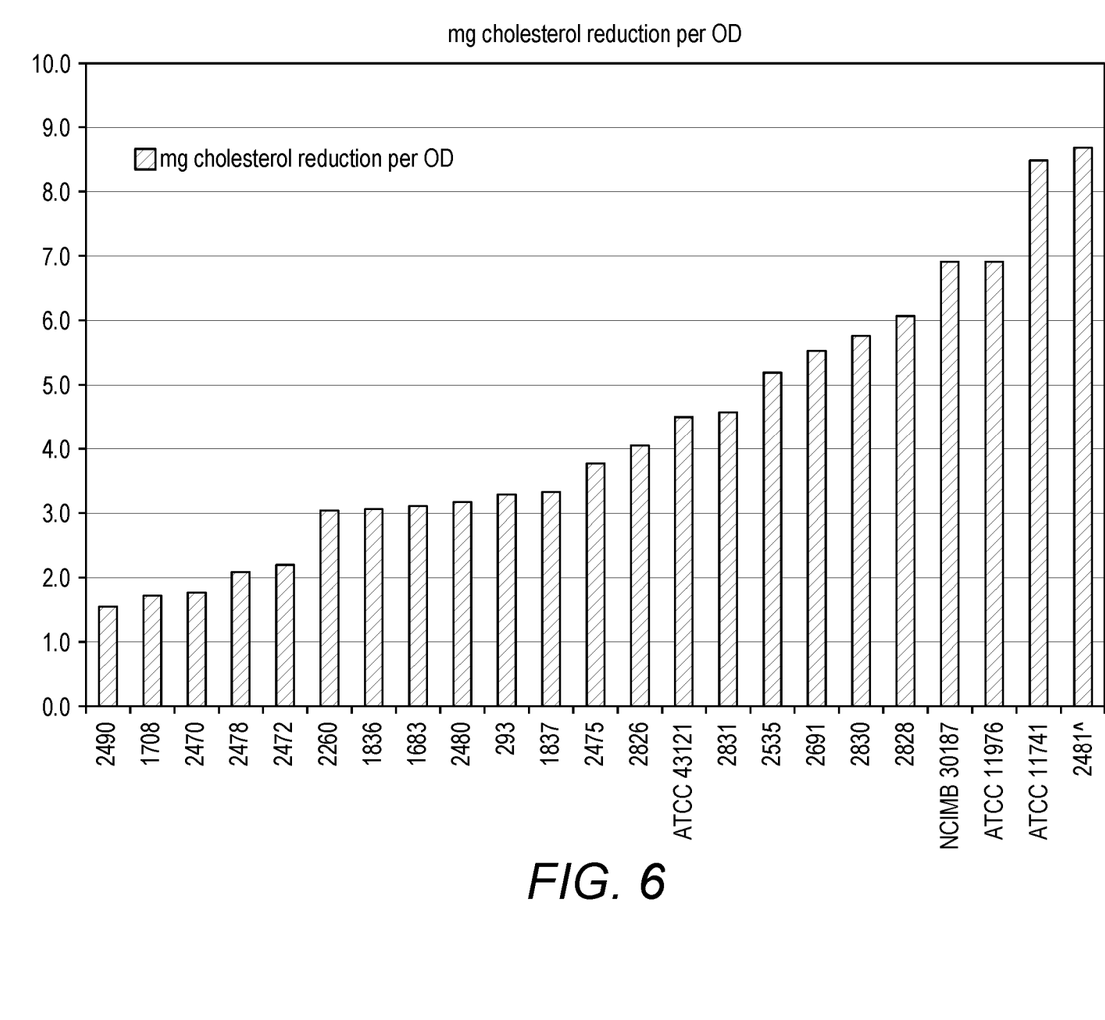
FIG. 6 is a bar chart showing the results of the 24 strains shown in FIG. 5 after normalizing cholesterol assimilation to the optical density.

Table 4 below and FIG. 6 shows the normalized cholesterol assimilation relative to the optical density.

TABLE 4

| Strain | Biological replicate 1 OD after 24 hours growth | Biological replicate 2 OD after 24 hours growth | Biological replicate 1 Cholesterol in mg/l | Biological replicate 2 Cholesterol in mg/l | Biological replicate 1 mg reduction per OD | Biological replicate 2 mg reduction per OD | Average mg cholesterol reduction per OD |
|---|---|---|---|---|---|---|---|
| 306 | 1.58 | 1.45 | 21.0 | 19.6 | 0.8 | 1.8 | 1.3 |
| 2490 | 1.31 | 1.28 | 19.1 | 21.5 | 2.5 | 0.6 | 1.5 |
| 1708 | 2.2 | 1.9 | 18.1 | 19.4 | 1.9 | 1.5 | 1.7 |
| 2471 | 1.55 | 1.53 | 19.7 | 19.4 | 1.6 | 1.9 | 1.8 |
| 2478 | 1.56 | 1.5 | 19.0 | 19.2 | 2.1 | 2.1 | 2.1 |
| 2472 | 1.66 | 1.95 | 19.0 | 17.6 | 2.0 | 2.4 | 2.2 |
| 2260 | 3.52 | 3.62 | 11.5 | 11.3 | 3.1 | 3.0 | 3.0 |
| 1836 | 3.61 | 3.75 | 9.7 | 12.3 | 3.5 | 2.7 | 3.1 |
| 1683 | 4.28 | 3.92 | 10.6 | 8.6 | 2.7 | 3.5 | 3.1 |
| 2480 | 1.2 | 1.04 | 19.3 | 18.3 | 2.5 | 3.9 | 3.2 |
| 293 | 3.54 | 3.27 | 10.8 | 11.4 | 3.3 | 3.3 | 3.3 |
| 1837 | 3.6 | 3.72 | 10.1 | 10.0 | 3.4 | 3.3 | 3.3 |
| 2475 | 0.72 | 0.75 | 19.1 | 20.0 | 4.5 | 3.1 | 3.8 |
| 2826 | 3.28 | 4.36 | 7.3 | 6.8 | 4.6 | 3.5 | 4.0 |
| ATCC 43121 | 3.15 | 4.52 | 6.4 | 4.4 | 5.0 | 3.9 | 4.5 |
| 2831 | 3.75 | 3.81 | 4.5 | 5.5 | 4.7 | 4.4 | 4.6 |
| 2535 | 2.65 | 2.62 | 9.1 | 8.1 | 5.0 | 5.4 | 5.2 |
| 2691 | 3.12 | 2.68 | 7.1 | 5.7 | 4.9 | 6.2 | 5.5 |
| 2830 | 3.22 | 2.84 | 5.3 | 4.5 | 5.3 | 6.3 | 5.8 |
| 2828 | 3.4 | 3.02 | na* | 4.0 |  | 6.1 | 6.1 |
| NCIMB 30187 | 2.75 | 2.58 | 3.5 | 4.3 | 6.8 | 7.0 | 6.9 |
| ATCC 11976 | 1.37 | 1.44 | 2.63 | 6.77 | 8.6 | 5.3 | 6.9 |
| ATCC 11741 | 1.24 | 1.33 | 3.43 | 3.50 | 8.8 | 8.2 | 8.5 |
| 2481^ | 1.45 | 1.42 | 1.0 | 18.4 | 14.7 | 2.7 | 8.7 |

An assessment was then made comparing the results of the strains based in % cholesterol reduction (table 5 below) and cholesterol reduction normalised to OD (table 6 below) in the context of their potential growth efficacy in the gut.

TABLE 5 sorted by "% cholesterol reduction"

| Strain | Average % cholesterol reduction | Average mg cholesterol reduction per OD | BSH activity; week 27 (some strains did not grow - na) | | | | BSH activity - week 30 | | | | L. species |
|---|---|---|---|---|---|---|---|---|---|---|---|
| | | | TDCA | GDCA | 0.5 Oxgal | 2 oxgal | TDCA | GDCA | 0.5 Oxgal | 2 oxgal | |
| 306 | 8.9 | 1.3 | 0 | 0 | 0 | 0 | 0 | 2 | 1 | 1 | brevis |
| 2490 | 9.1 | 1.5 | 0 | 2 | 0 | 0 | 0 | 2 | 0 | 0 | plantarum |
| 2471 | 12.2 | 1.8 | 0 | 2 | 0 | 0 | 0 | 0 | 1 | 1 | plantarum |
| 2475 | 12.4 | 3.8 | 0 | 0 | 0 | 0 | 0 | 3 | 1 | 1 | plantarum |
| 2478 | 14.3 | 2.1 | 0 | 0 | 0 | 0 | 0 | 2 | 1 | 1 | plantarum |
| 2480 | 15.7 | 3.2 | 0 | 0 | 0 | 0 | 0 | 2 | 1 | 1 | plantarum |
| 1708 | 15.9 | 1.7 | 0 | 1 | 0 | 0 | 0 | 3 | 0 | 0 | brevis |
| 2472 | 17.9 | 2.2 | 0 | 2 | 0 | 0 | 0 | 2 | 0 | 0 | plantarum |
| 2260 | 48.7 | 3.0 | 0 | 3 | 1 | 0 | 0 | 3 | 0 | 0 | plantarum |
| 293 | 50.2 | 3.3 | 0 | 0 | 1 | 0 | 0 | 3 | 3 | 3 | brevis |
| 1836 | 50.5 | 3.1 | 0 | 1 | 1 | 0 | 0 | 1 | 1 | 1 | plantarum |
| 1837 | 54.7 | 3.3 | 0 | 2 | 1 | 0 | 0 | 3 | 1 | 1 | plantarum |
| 2481 | 56.3 | 8.7 | 0 | 2 | 0 | 0 | 0 | 2 | 1 | 1 | plantarum |
| 1683 | 56.9 | 3.1 | 0 | 3 | 1 | 0 | 0 | 3 | 0 | 0 | plantarum |
| 2535 | 61.4 | 5.2 | 0 | 0 | 1 | 0 | 0 | 3 | 0 | 0 | plantarum |
| ATCC 11976 | 67.3 | 6.9 | 0 | 0 | 0 | 0 | 0 | 0 | 0 | 0 | fermentum |
| 2826 | 68.2 | 4.0 | 0 | 3 | 1 | 0 | 0 | 3 | 0 | 0 | plantarum |
| 2691 | 71.3 | 5.5 | 0 | 0 | 1 | 0 | 0 | 3 | 0 | 0 | plantarum |
| ATCC43121 | 75.7 | 4.5 | 3 | 0 | 2 | 1 | 3 | 0 | 0 | 0 | acidophilus |
| ATCC 11741 | 75.9 | 8.5 | na | na | na | na | 0 | 0 | 0 | 0 | salivarius |
| 2831 | 77.5 | 4.6 | na | na | na | na | 0 | 3 | 0 | 0 | plantarum |
| 2830 | 77.9 | 5.8 | 0 | 0 | 1 | 0 | 0 | 3 | 0 | 0 | plantarum |
| 2828 | 82.2 | 6.1 | 0 | 3 | 1 | 0 | 0 | 3 | 0 | 0 | plantarum |
| NCIMB 30187 | 82.6 | 6.9 | na | na | na | na | na | na | na | na | plantarum |

(interesting candidates are underlined)

TABLE 6 sorted by "mg cholesterol reduction normalized to OD"

| Strain | Average % cholesterol reduction | Average mg cholesterol reduction per OD | BSH activity; week 27 (some strains did not grow - na) | | | | BSH activity - week 30 | | | | L. species |
|---|---|---|---|---|---|---|---|---|---|---|---|
| | | | TDCA | GDCA | 0.5 Oxgal | 2 oxgal | TDCA | GDCA | 0.5 Oxgal | 2 oxgal | |
| 306 | 8.9 | 1.3 | 0 | 0 | 0 | 0 | 0 | 2 | 1 | 1 | brevis |
| 2490 | 9.1 | 1.5 | 0 | 2 | 0 | 0 | 0 | 2 | 0 | 0 | plantarum |
| 1708 | 15.9 | 1.7 | 0 | 1 | 0 | 0 | 0 | 3 | 0 | 0 | brevis |
| 2471 | 12.2 | 1.8 | 0 | 2 | 0 | 0 | 0 | 0 | 1 | 1 | plantarum |
| 2478 | 14.3 | 2.1 | 0 | 0 | 0 | 0 | 0 | 2 | 1 | 1 | plantarum |
| 2472 | 17.9 | 2.2 | 0 | 2 | 0 | 0 | 0 | 2 | 0 | 0 | plantarum |
| 2260 | 48.7 | 3.0 | 0 | 3 | 1 | 0 | 0 | 3 | 0 | 0 | plantarum |
| 1836 | 50.5 | 3.1 | 0 | 1 | 1 | 0 | 0 | 1 | 1 | 1 | plantarum |
| 1683 | 56.9 | 3.1 | 0 | 3 | 1 | 0 | 0 | 3 | 0 | 0 | plantarum |
| 2480 | 15.7 | 3.2 | 0 | 0 | 0 | 0 | 0 | 2 | 1 | 1 | plantarum |
| 293 | 50.2 | 3.3 | 0 | 0 | 1 | 0 | 0 | 3 | 3 | 3 | brevis |
| 1837 | 54.7 | 3.3 | 0 | 2 | 1 | 0 | 0 | 3 | 1 | 1 | plantarum |
| 2475 | 12.4 | 3.8 | 0 | 0 | 0 | 0 | 0 | 3 | 1 | 1 | plantarum |
| 2826 | 68.2 | 4.0 | 0 | 3 | 1 | 0 | 0 | 3 | 0 | 0 | plantarum |
| ATCC43121 | 75.7 | 4.5 | 3 | 0 | 2 | 1 | 3 | 0 | 0 | 0 | acidophilus |
| 2831 | 77.5 | 4.6 | na | na | na | na | 0 | 3 | 0 | 0 | plantarum |
| 2535 | 61.4 | 5.2 | 0 | 0 | 1 | 0 | 0 | 3 | 0 | 0 | plantarum |
| 2691 | 71.3 | 5.5 | 0 | 0 | 1 | 0 | 0 | 3 | 0 | 0 | plantarum |
| 2830 | 77.9 | 5.8 | 0 | 0 | 1 | 0 | 0 | 3 | 0 | 0 | plantarum |
| 2828 | 82.2 | 6.1 | 0 | 3 | 1 | 0 | 0 | 3 | 0 | 0 | plantarum |
| NCIMB 30187 | 82.6 | 6.9 | na | na | na | na | na | na | na | na | plantarum |
| ATCC 11976 | 67.3 | 6.9 | 0 | 0 | 0 | 0 | 0 | 0 | 0 | 0 | fermentum |
| ATCC 11741 | 75.9 | 8.5 | na | na | na | na | 0 | 0 | 0 | 0 | salivarius |
| 2481 | 56.3 | 8.7 | 0 | 2 | 0 | 0 | 0 | 2 | 1 | 1 | plantarum |

(interesting candidates are underlined)

Strains 2828 (ECGC 13110403), 2830 (ECGC 13110402), 2691 (ECGC 13110401) and ATCC43121 show high cholesterol reduction and good BSH activity in both analysis above in tables 5 and 6. The in vitro tests conducted strongly suggest that these strains, whether in combination with one another or individually, would be suitable for use in modifying the absorption of cholesterol or in the treatment of heart disease, diabetes or obesity in an individual. These strains could be used in conjunction with growth specific prebiotics to encourage and support growth.

Experiments were then conducted to look at how well a number of strains coped with being freeze dried and also the subsequent BSH activity towards specific bile salts of three selected strains.

The first step was to ferment a number of strains. Strains were found to acidify all carriers and cryoprotectants chosen. It was assessed that formulations should be worked cold during production. The choice of carriers and their final concentrations were as follows: 82% MD+14% Sorbitol (MD=maltodextrin) (rest medium, and bacteria) and 82% MD+14% Sucrose. All strains grew well on the Nitrogen sources selected with a mix of Yeast extract and Soy peptone. No animal ingredients were suggested for the validation, but it was assessed that the soy peptone may cause insoluble precipitate, which could hinder the downstream processing in the future. Ideally, it was assessed that the medium to be used in production is based on 100% YE, with no other Nitrogen sources. Table 7 below shows the summary of the results of the fermentation and viability rates for the three chosen strains (B4321, B2828 and B2830) in the media. In the following data, B4321 relates to the same strain as B2691 referred to earlier.

TABLE 7

| | Strain | | | | | |
|---|---|---|---|---|---|---|
| | B4321 (B2691) | | B2828 | | B2830 | |
| | Media | | | | | |
| | Sorbitol | Sucrose | Sorbitol | Sucrose | Sorbitol | Sucrose |
| Coagulation | YES | | NO | | NO | |
| ODmax-fermentation | 9.5 | | 12.9 | | 15.7 | |
| CFU-fermentation | 7.5E+09 | | 1.4E+10 | | 1.6E+10 | |
| Cells/OD | 8E+08 | | 1E+09 | | 1E+09 | |
| Conversion factor in Carrier | 24% | 24% | 18% | 17% | 14% | 14% |
| CFU in Carrier solution (30% DM) | 3.9E+09 | 4.1E+09 | 2.1E+09 | 2.5E+09 | 1.8E+09 | 2.2E+09 |
| CFU in powder | 3.24E+09 | 4.12E+09 | 2.35E+09 | 2.82E+09 | 1.38E+09 | 2.62E+09 |
| Survival freeze drying | 28% | 34% | 39% | 39% | 27% | 41% |

Figure 7:
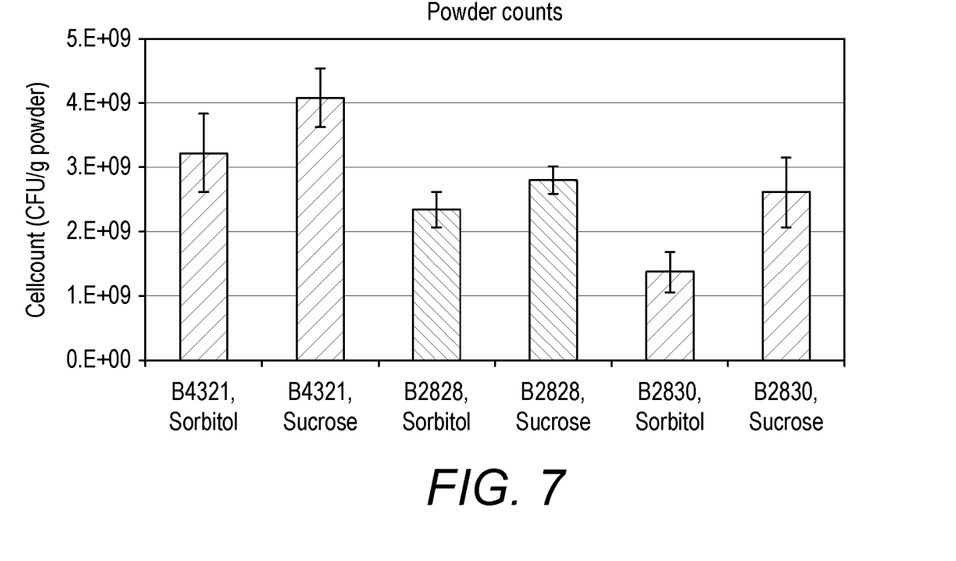
FIG. 7 is a bar chart showing the powder count of a number of strains during the freeze drying experiments.
Figure 8:
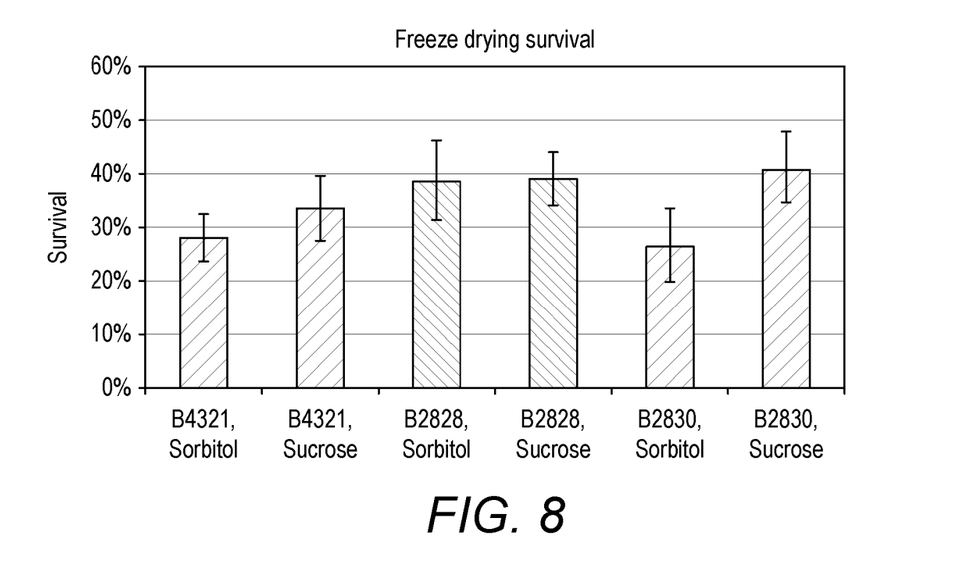
FIG. 8 is a bar chart showing the freeze drying survival of a number of strains during the freeze drying experiments.

FIG. 7 shows the powder counts for a number of strains, whereas FIG. 8 shows the freeze drying survival of those same strains.

Figure 9:
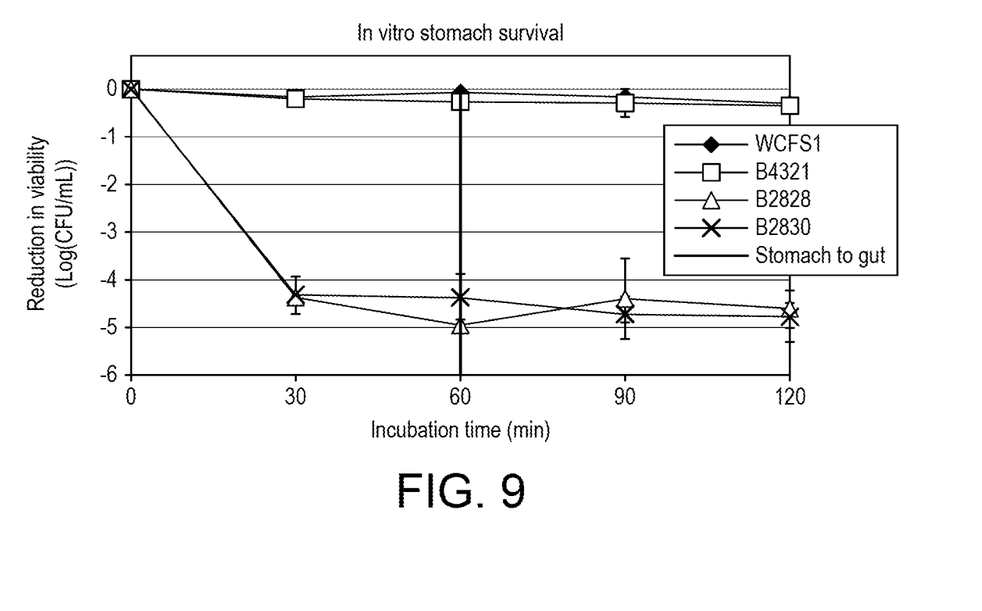
FIG. 9 is a bar chart showing the in vitro stomach survival of a number of strains which had been freeze dried.

FIG. 9 shows the survival of the strains in the stomach. Strain B4321 (B2691) clearly survives better under the conditions tested ~109 CFU/mL Stationary cells incubated for 60 min at pH 2.45 in a Na/K/HCl solution with Pepsin adn lipase.

Figure 10:
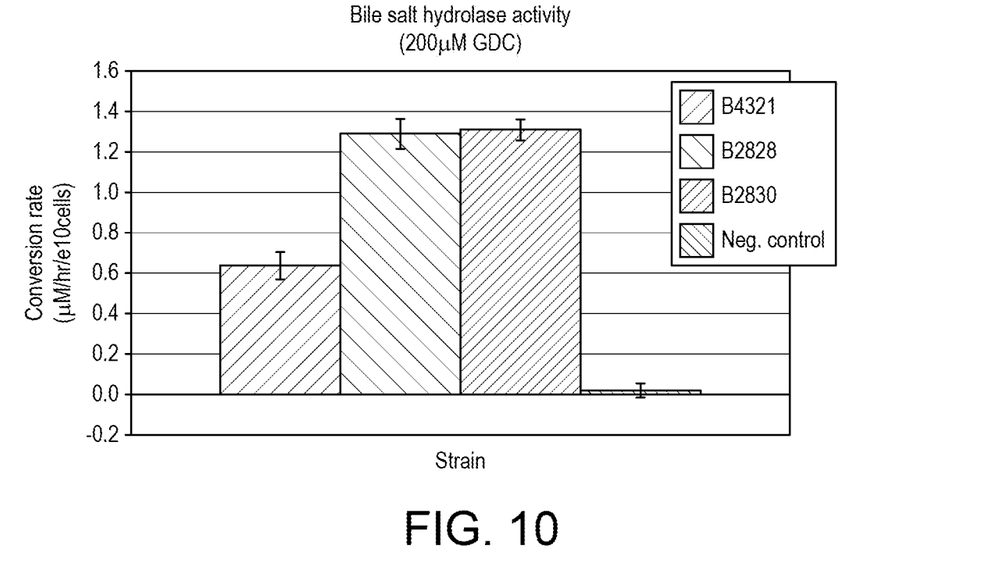
FIG. 10 is a bar chart showing the bile salt hydrolase activity at 200 µM GDC for strains B4321, B2828 and B2830.
Figure 11:
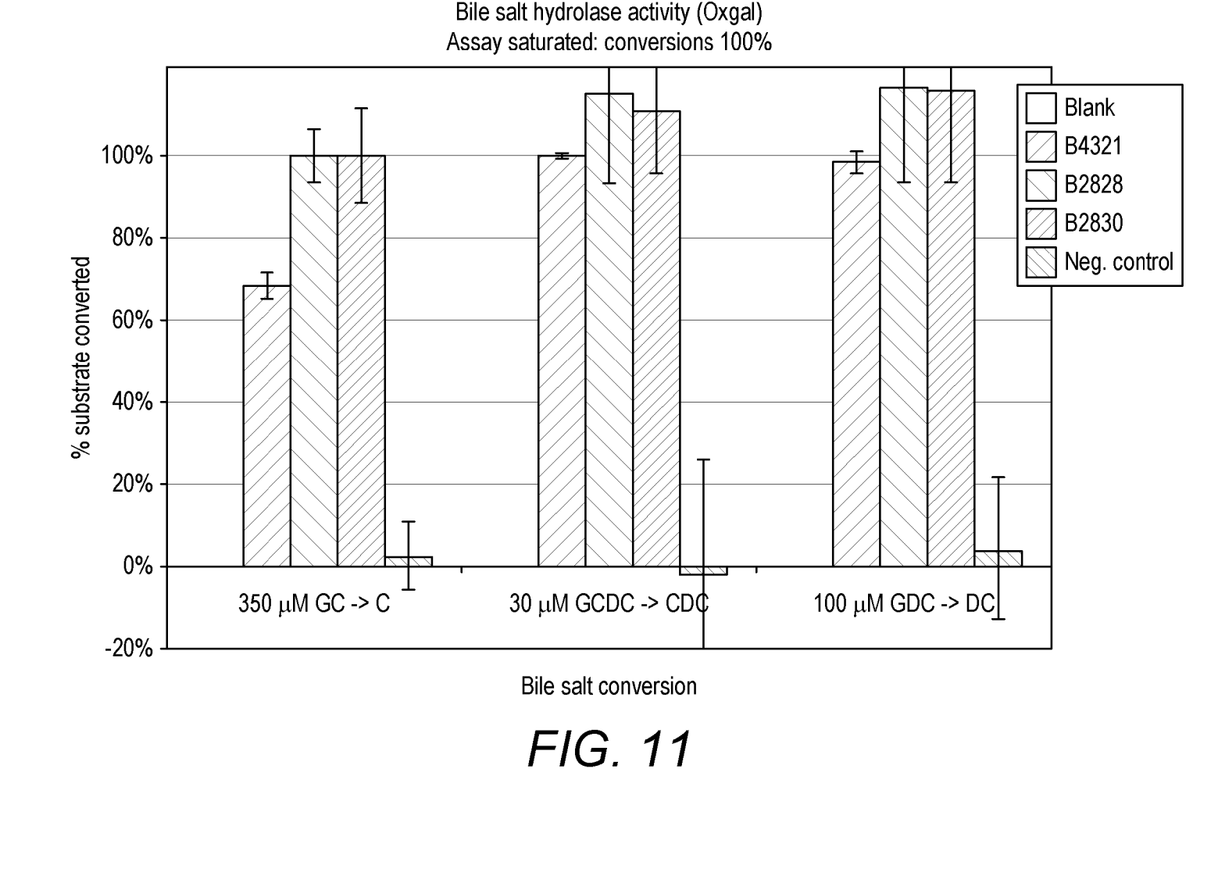
FIG. 11 is a bar chart showing the bile salt hydrolase activity (Oxgal) for strains B4321, B2828 and B2830.

FIGS. 10 and 11 show the Bile Salt Hydrolase activity on the chosen strains. B2828 and B2830 converted nearly 100% of the substrate in 3 hrs. Therefore no discrimination appeared to be possible between these strains.

The forgoing embodiments are not intended to limit the scope of the protection afforded by the claims, but rather to describe examples of how the invention may be put into practice.

Deposition of Biological Material

A deposition of biological material was made for the purposes of a United Kingdom patent application at the National Collection of Type Cultures (NCTC) in the UK. The NCTC is a recognised International Depository Authority (IDA) under the Budapest Treaty.

Each of the strains deposited at the NCTC in the UK have been assigned a number with the prefix ECGC. ECGC stands for European Culture General Collection.

It should be noted that B2691 (ECGC 13110401) was originally phenotypically classified as a *L. reteri* upon deposition at the NCTC. It has subsequently been found to be a *L. plantarum* based upon genetic analysis and this strain is referred to in this application as B2691 and renamed B4321 in later experiments.

The invention claimed is:

1. A method of treating an individual with elevated cholesterol serum levels by administering a composition having an effective amount of *Lactobacillus plantarum* 2830 deposited at the United Kingdom National Collection of Type Cultures under ECGC 13110402.

2. The method of claim 1, wherein the strain is administered in an amount in the range of $10^5$ cfu/g to $10^{12}$ cfu/g.

3. The method of claim 1, wherein the composition is encapsulated.

4. The method of claim 1, wherein the strain is mixed with a prebiotic composition.

5. The method of claim 4, wherein the prebiotic comprises a prebiotic specific for the growth of the strain.

6. The method of claim 1, wherein the composition is in the form of a food stuff.

7. The method of claim 1, wherein the composition is in the form of a dietary supplement.

8. A composition comprising at least one of the strains selected from *Lactobacillus plantarum* 2828 deposited at the United Kingdom National Collection of Type Cultures under ECGC 13110403; *Lactobacillus plantarum* 2830 deposited at the United Kingdom National Collection of Type Cultures under ECGC 13110402; and *Lactobacillus plantarum* 2691 deposited at the United Kingdom National Collection of Type Cultures under ECGC 13110401; for use in the modification of the absorption of cholesterol or for use in the treatment of high cholesterol, heart disease, diabetes, or obesity.

9. The composition of claim 8, wherein the composition further comprises the strain *Lactobacillus acidophilus* ATCC 43121.

10. The composition of claim 8, wherein the composition comprises two or more strains selected from *Lactobacillus plantarum* 2828 deposited at the United Kingdom National Collection of Type Cultures under ECGC 13110403; *Lactobacillus plantarum* 2830 deposited at the United Kingdom National Collection of Type Cultures under ECGC 13110402; *Lactobacillus plantarum* 2691 deposited at the United Kingdom National Collection of Type Cultures under ECGC 13110401; and *Lactobacillus acidophilus* ATCC 43121.

11. The composition of claim 8, wherein the strain or strains is/are in an amount in the range of $10^5$ cfu/g to $10^{12}$ cfu/g.

12. The composition of claim 8, wherein the composition is encapsulated.

13. The composition of claim 8, wherein the strain or strains is/are mixed with a prebiotic composition.

14. The composition of claim 13, wherein the prebiotic comprises a prebiotic specific for the growth of the strain or strains.

15. The composition of claim 8, wherein the composition is in the form of a food stuff.

16. The composition of claim 8, wherein the composition is in the form of a dietary supplement.

\* \* \* \* \*